(12) United States Patent
Guttmann

(10) Patent No.: US 7,385,027 B2
(45) Date of Patent: Jun. 10, 2008

(54) MEMBRANE-PERMEABLE PEPTIDE CAPABLE OF CALPAIN INHIBITION

(75) Inventor: Rodney Guttmann, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 491 days.

(21) Appl. No.: 10/751,658

(22) Filed: Jan. 6, 2004

(65) Prior Publication Data
US 2004/0248795 A1 Dec. 9, 2004

Related U.S. Application Data

(60) Provisional application No. 60/438,318, filed on Jan. 7, 2003.

(51) Int. Cl.
C07K 7/00 (2006.01)
C12N 9/99 (2006.01)

(52) U.S. Cl. .......... 530/330; 435/184; 930/250

(58) Field of Classification Search .......... None
See application file for complete search history.

(56) References Cited

U.S. PATENT DOCUMENTS 5,554,767 A 9/1996 Wang et al.
5,622,967 A 4/1997 Dolle et al.
6,015,787 A 1/2000 Potter et al.
6,103,720 A 8/2000 Lubisch et al.
6,117,680 A * 9/2000 Natesan et al. .......... 435/455
6,294,518 B1 9/2001 Potter et al.

FOREIGN PATENT DOCUMENTS

WO WO 98/46250 * 10/1998
WO WO 99/57149 * 11/1999

OTHER PUBLICATIONS

Guttman et al., Biochem Biophys Res Comm. 333: 1087-1092, 2005.*
Wells et al. Biochemistry 29: 8509-8517, 1990.*
Ngo et al. The Protein Folding Problem and Tertiary Structure Prediction, 492-495, 1994.*
Bork et al. Genome Res 10: 398-400, 2000.*
Skolnick et al. Trends in Biothech 18: 34-39, 2000.*
Doerks et al. Trends in Genetics 14: 248-250, 1998.*
Smith et al. Nature Biotechnology 15: 1222-1223, 1997.*
Brenner SE, Trends in Genetics 15: 132-133, 1999.*
Bork et al. Trends in Genetics 12: 425-427, 1996.*

* cited by examiner

*Primary Examiner*—Gary Nickol
*Assistant Examiner*—Aditi Dutt
(74) *Attorney, Agent, or Firm*—McDermott Will & Emery LLP

(57) ABSTRACT

5-mer peptides that can inhibit calpain I and calpain II are disclosed. The peptide sequence is as follows: Leu or Ala)-(Xaa)-(Asp or Glu)-(Xaa)-(Leu or Met), where Xaa can be any amino acid.

3 Claims, 3 Drawing Sheets

```
                            SEQUENCE LISTING

<160> NUMBER OF SEQ ID NOS: 18

<210> SEQ ID NO 1
<211> LENGTH: 5
<212> TYPE: PRT
<213> ORGANISM: Homo sapiens

<400> SEQUENCE: 1

Leu Ser Glu Ala Leu
1               5

<210> SEQ ID NO 2
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is L or A
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is D or E
<220> FEATURE:
<221> NAME/KEY: MISC_FEATURE
<222> LOCATION: (4)..(4)
<223> OTHER INFORMATION: X is any amino acid
<220> FEATURE:
<221> NAME/KEY: MISC_FEATURE
<222> LOCATION: (5)..(5)
<223> OTHER INFORMATION: X is L or M

<400> SEQUENCE: 2

Xaa Xaa Xaa Xaa Xaa
1               5

<210> SEQ ID NO 3
<211> LENGTH: 5
<212> TYPE: PRT
<213> ORGANISM: Homo sapiens

<400> SEQUENCE: 3

Leu Ser Glu Ala Leu
1               5

<210> SEQ ID NO 4
<211> LENGTH: 5
<212> TYPE: PRT
<213> ORGANISM: Homo sapiens

<400> SEQUENCE: 4

Leu Ala Asp Ala Leu
1               5

<210> SEQ ID NO 5
<211> LENGTH: 5
<212> TYPE: PRT
<213> ORGANISM: Homo sapiens
```

```
<400> SEQUENCE: 5

Leu Phe Glu Ala Leu
1               5

<210> SEQ ID NO 6
<211> LENGTH: 5
<212> TYPE: PRT
<213> ORGANISM: Homo sapiens

<400> SEQUENCE: 6

Leu Tyr Asp Ala Leu
1               5

<210> SEQ ID NO 7
<211> LENGTH: 5
<212> TYPE: PRT
<213> ORGANISM: Homo sapiens

<400> SEQUENCE: 7

Leu Leu Glu Ala Leu
1               5

<210> SEQ ID NO 8
<211> LENGTH: 5
<212> TYPE: PRT
<213> ORGANISM: Homo sapiens

<400> SEQUENCE: 8

Leu Arg Asp Ala Leu
1               5

<210> SEQ ID NO 9
<211> LENGTH: 5
<212> TYPE: PRT
<213> ORGANISM: Homo sapiens

<400> SEQUENCE: 9

Leu Tyr Asp Ala Met
1               5

<210> SEQ ID NO 10
<211> LENGTH: 5
<212> TYPE: PRT
<213> ORGANISM: Homo sapiens

<400> SEQUENCE: 10

Leu Thr Asp Ala Leu
1               5

<210> SEQ ID NO 11
<211> LENGTH: 5
<212> TYPE: PRT
<213> ORGANISM: Homo sapiens

<400> SEQUENCE: 11

Ala Leu Asp Ala Leu
1               5

<210> SEQ ID NO 12
<211> LENGTH: 5
<212> TYPE: PRT
<213> ORGANISM: Homo sapiens

<400> SEQUENCE: 12
```

-continued

```
Leu Leu Asp Ala Leu
1               5

<210> SEQ ID NO 13
<211> LENGTH: 5
<212> TYPE: PRT
<213> ORGANISM: Homo sapiens

<400> SEQUENCE: 13

Pro Ile Asp Ala Leu
1               5

<210> SEQ ID NO 14
<211> LENGTH: 5
<212> TYPE: PRT
<213> ORGANISM: Homo sapiens

<400> SEQUENCE: 14

Leu Ile Asp Glu Leu
1               5

<210> SEQ ID NO 15
<211> LENGTH: 5
<212> TYPE: PRT
<213> ORGANISM: Homo sapiens

<400> SEQUENCE: 15

Ala Ile Asp Ala Leu
1               5

<210> SEQ ID NO 16
<211> LENGTH: 5
<212> TYPE: PRT
<213> ORGANISM: Homo sapiens

<400> SEQUENCE: 16

Leu Ile Asp Thr Leu
1               5

<210> SEQ ID NO 17
<211> LENGTH: 5
<212> TYPE: PRT
<213> ORGANISM: Homo sapiens

<400> SEQUENCE: 17

Leu Ala Asp Ser Leu
1               5

<210> SEQ ID NO 18
<211> LENGTH: 5
<212> TYPE: PRT
<213> ORGANISM: Homo sapiens

<400> SEQUENCE: 18

Leu Ser Asp Ser Leu
1               5
```

MEMBRANE-PERMEABLE PEPTIDE CAPABLE OF CALPAIN INHIBITION

CROSS-REFERENCE TO RELATED APPLICATION

This application claims priority to provisional application 60/438,318, filed Jan. 7, 2003.

FIELD OF THE INVENTION

The invention pertains to peptides that are membrane-permeable and effective at protecting neurons against calpain-mediated cell death. In particular, the peptides of the invention are similar to domains A and C of calpastatin, which is a known inhibitor of calpain I and calpain II. However, unlike calpastatin, the peptides of the invention do not target an active cysteine of calpain.

BACKGROUND OF THE INVENTION

Calpain is a cytosolic calcium-dependent cysteine protease. It is found in all mammalian tissue and cell types. The calpain family of proteases consists of two recognized proteins.

The first member of the calpain family is calpain I or µ-calpain which is the high sensitivity form and is activated by a low calcium concentration (2-75 µM). Calpain I is concentrated in synapses and neuronal cell bodies.

The second member of the calpain family is calpain II or m-calpain. It has a ribbon like structure and is the lower sensitivity form. It is activated by higher concentrations of calcium (200-800 µM). Calpain II is the dominant form.

Calpastatin is a known endogenous inhibitor of calpain I and calpain II. It has four internally repeated domains, each of which independently binds a calpain molecule in its active, $Ca^{++}$-bound conformation with high affinity.

Calpains play an important role in various physiological processes. These processes include, inter alia, the cleavage of regulatory proteins such as protein kinase C (PKC) and degradation of cytoskeletal or microtubule-associated proteins (MAP) such as tau. Research has demonstrated that calpain inhibitors have improved recovery from the memory performance deficits and neuromotor disturbances. Calpain inhibitors inhibit the release of the 13-AP4 protein. Therefore, it has been suggested that they have a potential use as therapeutic agents in Alzheimer's disease. Calpain inhibitors have also had a protective effect on hypoxia-damaged kidneys and have had favorable effects following cardiac damage produced by ischemias of the heart (e.g., myocardial infarction) or reperfusion. It has also been found that calpain inhibitors have cytotoxic effects on tumor cells. Elevated calpain levels are also implicated in the pathophysiology of cerebral ischemia, platelet activation, NF-KB activation, muscular dystrophy, cataract progression and rheumatoid arthritis. with various pathophysiological processes such as, inflammations, muscular dystrophies, cataracts of the eyes, and injuries to the central nervous system (e.g., trauma).

Calpains reside in the cytosol of cells and are activated by $Ca^{++}$ at a physiological pH. Its proteolytic activity appears to be selective against certain target proteins, such as components of the cytoskeleton and calmodulin-dependent enzymes.

Excessive excitation by a neurotransmitter glutamate can lead to death of nerve cells (neurons) and neurodegeneration. It is believed that toxic effects of glutamate comes from overactivation of its target glutamate receptors (e.g., under ischemic conditions or stroke). This in turn produces an influx of calcium ion ($Ca^{++}$) into the neurons. The rise of cellular $Ca^{++}$ level triggers the activation of calpain I. Calpain I then goes on to degrade cytoskeletal protein such as spectrin, which is believed to disrupt normal cellular functions, and eventually leads to cell death.

SUMMARY OF THE INVENTION

The invention is directed to proteins and methods of using the proteins that inhibit calpains I and II. The method includes contacting the cell with an effective amount of the protein for inhibiting calpains I and II.

In one aspect of the invention there is provided a peptide comprising an amino acid sequence (Leu or Ala)-(Xaa)-(Asp or Glu)-(Xaa)-(Leu or Met), where Xaa is any amino acid (SEQ ID NO:2). In a preferred embodiment the peptide has the amino acid sequence, Leu-Ser-Glu-Ala-Leu (LSEAL).

In a another aspect of the invention there is provided a method for inhibiting calpain comprising contacting a cell with an amount of a peptide comprising the amino acid sequence (Leu or Ala)-(Xaa)-(Asp or Glu)-(Xaa)-(Leu or Met), where Xaa is any amino acid (SEQ ID NO:2).

In yet another aspect of the invention there is provided a method for inhibiting calpain-dependent cell death comprising contacting a cell with an effective amount of a cell membrane permeable peptide comprising the sequence (Leu or Ala)-(Xaa)-Asp or Glu)-(Xaa)-(Leu or Met), where Xaa is any amino acid (SEQ ID NO:2).

The invention also provides a method for protecting cells from UV irradiation-induced cell death comprising exposing the cells to an effective amount of a polypeptide having the amino acid sequence, (Leu or Ala)-(Xaa)-(Asp or Glu)-(Xaa)-(Leu or Met), where Xaa is any amino acid (SEQ ID NO:2).

Other objects, features and advantages of this invention will become apparent upon reading the following detailed description and referring to the accompanying drawings.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings.

DETAILED DESCRIPTION OF THE INVENTION

Figure 1:
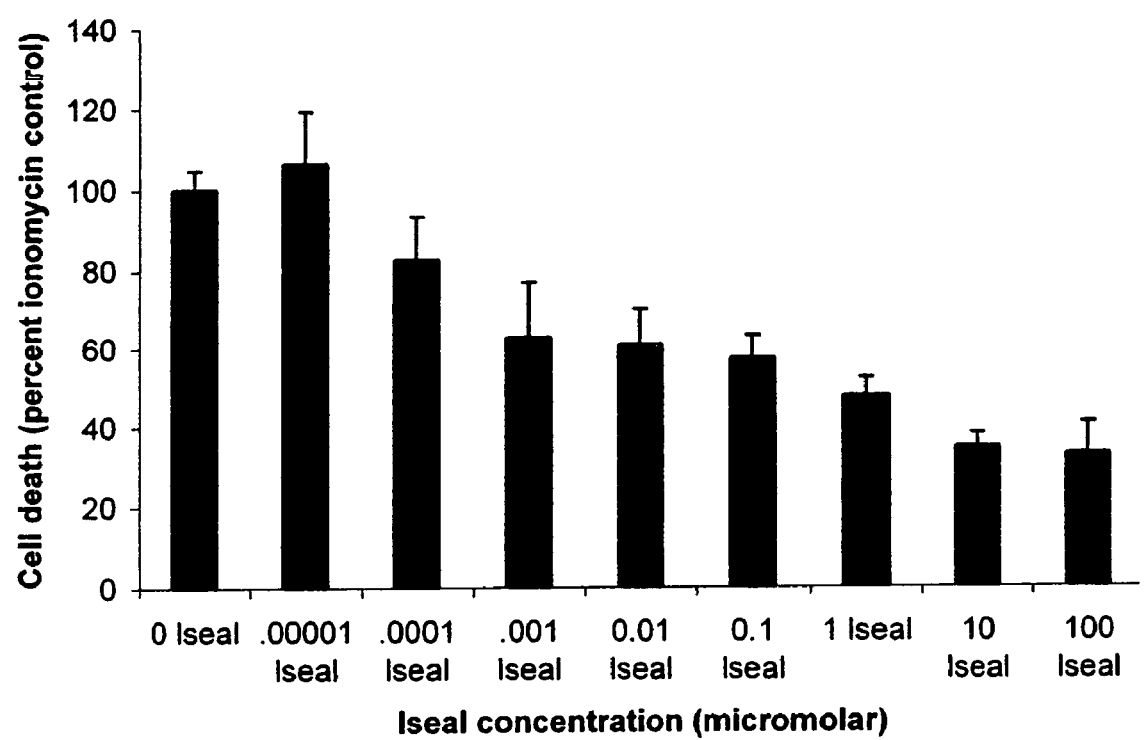
FIG. 1 is a graphical illustration of the relationship of dose response of Leu-Ser-Glu-Ala-Leu (LSEAL) (SEQ ID NO. 3) with ionomycin (ionomycin toxicity) with respect to cell death.

This invention relates to 5-mer peptides and methods of using these peptides for inhibiting calpain. In particular, the peptides comprise the following sequence: (Leu or Ala)-(Xaa)-(Asp or Glu)-(Xaa)-(Leu or Met), where Xaa can be any amino acid (SEQ ID NO. 2).

In one embodiment, Xaa is selected from the group consisting of Ala, Arg, Ile, Leu, Pro, Phe, Ser, Thr and Tyr.

In another embodiment, the peptides include Leu-Ser-Glu-Ala-Leu (SEQ ID NO:3), Leu-Ala-Asp-Ala-Leu (SEQ ID NO:4), Leu-Phe-Glu-Ala-Leu (SEQ ID NO:5), Leu-Tyr-Asp-Ala-Leu (SEQ ID NO:6), Leu-Leu-Glu-Ala-Leu (SEQ ID NO:7), Leu-Arg-Asp-Ala-Leu (SEQ ID NO:8), Leu-Tyr-Asp-Ala-Met (SEQ ID NO:9), Leu-Thr-Asp-Ala-Leu (SEQ ID NO:10), Ala-Leu-Asp-Ala-Leu (SEQ ID NO:11), Leu-Leu-Asp-Ala-Leu (SEQ ID NO: 12), Pro-Ile-Asp-Ala-Leu (SEQ ID NO:13) Leu-Ile-Asp-Glu-Leu (SEQ ID NO:14), Ala-Ile-Asp-Ala-Leu (SEQ ID NO:15), Leu-Ile-Asp-Thr-Leu (SEQ ID NO:16), Leu-Ala-Asp-Ser-Leu (SEQ ID NO:17), and Leu-Ser-Asp-Ser-Leu (SEQ ID NO:18). All of these amino acid sequences are similar to the binding region of the endogenous inhibitor calpastatin.

One particular five amino acid peptide comprising Leu-Ser-Glu-Ala-Leu (SEQ ID NO. 3) (hereinafter LSEAL is particularly preferred for its ability to inhibit calpain activity both in vitro and in situ. It was found that this peptide is membrane-permeable and effective at protecting neurons against calpain-mediated cell death in two different paradigms.

LSEAL is similar to domains A and C of calpastatin which have been extensively studied by others in which they have shown that regions of calpastatin that are similar to our peptides are required for full inhibition of calpains. In addition, other groups have shown that mutations of specific amino acids in domains A or C, which are the equivalent amino acids in our peptide (SEQ ID NO. 3) of the present invention, result in reduced calpastatin inhibitory action, indicating that the sequence is likely optimal for calpain inhibition. These findings suggest that the peptides of the invention can mimic the actions of calpastatin.

The LSEAL peptide inhibits calpain activity in vitro towards the substrate tau protein. Also, this peptide prevents calpain-dependent cell death in two model systems of low-dose ionomycin treatment as well as UV-induced cell toxicity. While other synthetic inhibitors are available for calpains, this peptide has several advantages.

First, all other calpain inhibitors target the active site cysteine of calpain. This leads to significant specificity loss as many other proteases have cysteine residues at their active sites that have been shown to be modified by these other inhibitors. As such, it is extremely unlikely that the peptides will react with other proteases. The peptides of the invention mimics a key portion of the calpastatin molecule required for its endogenous and specific inhibitory action to the calpains.

Second, the peptides of the invention are membrane-permeable without the need for other modifications. The peptides of the present invention can affect changes inside a cell, and are likely to produce more specific effects due to calpain, and are more membrane-permeable than all previous calpain inhibitors.

The description below sets forth the method used to identify the peptide(s) using the Ph.D-12™ phage display system from New England Biolabs (NEB). The protocol for determining the number of phages is from the NEB Ph.D-12™ Kit manual, version 2.5. In this method, the active-site of calpain I was irreversibly inactivated or blocked with Calpain Inhibitor IV, and the peptide(s) were isolated as calcium-dependent binding peptides. Therefore, these peptides have a calpain I conformation-dependent binding sequence.

A mixture of 500 μL of Hepes balanced salt solution (HBSS) (2× concentration) was mixed with 475 μL distilled water, 20 μL of calpain I, 0.5 μL of calpain inhibitor IV and 5 μL of 200 mM $CaCl_2$. Calpain inhibitor IV was in a buffer containing 20 mM Hepes, 0.7 mM $Na_2HPO_4$, 137 mM NaCl, 5 mM KCl, 6 mM glucose at a pH 7.4 (1×HBSS) in the presence of 1 mM $CaCl_2$. The calpain inhibitor IV was added to permanently block the active cysteine of calpain I. $CaCl_2$ was added to activate the calpain I active site. A single well of a Nunc-Immuno™ microwell plate with a Maxi-iSorp™ surface was filled with 200 μL of the mixture and incubated at room temperature for 15 minutes. The plate was covered and shaken in an orbital shaker for 30 minutes at 37° C. and at 250 rpm.

The well was rinsed three times with a rinse solution comprising 1× concentration of HBSS and 1 mM $CaCl_2$ to remove excess and/or non-bound calpain I. To prevent direct binding of the phage to the Sample well, the well and a second well (hereinafter a control well) were treated with a blocking agent, a 3% bovine serum albumin (BSA) in 1×HBSS in 1 mM $CaCl_2$. The plate was then covered and shaken in the orbital shaker for 30 minutes at 37° C. and at 250 rpm. The control well and the Sample well were then rinsed three times with the rinse solution.

The phage (approximately $2 \times 10^{11}$ cells) were added to the control well. The plate was covered and shaken in the orbital shaker for 30 minutes at 37° C. and at 250 rpm. The phage were then transferred to the Sample well containing calpain I and the plate was covered and shaken in the orbital shaker for 30 minutes at 37° C. and at 250 rpm. After incubation, the plate was washed 50 times with the rinse solution to remove excess or non-bound phage. The final wash, i.e., the 50th wash, was saved and placed in a microtube.

In accordance with the protocol in the NEB instruction manual, the Sample well was eluted four times with HBSS and 1 mM ethyleneglycol-bis(β-aminoethylether)-N,N,N', N'-tetraacetic acid (EGTA), a calcium chelating agent. Each elution with EGTA was for a period of 10 to 15 minutes at room temperature and 60 rpm shaking. Each of the four elutions were saved. The well was then eluted with a solution containing 0.2 M glycine having a pH of 2.2, and then with 4M solution of urea. As for the elution with glycine, this step was performed for 5 minutes at room temperature followed by a neutralization step by adding 150 μL of 1M tris-HCl to raise the pH to 9.1 to prevent killing of the phage. The glycine and urea elutants were combined. Each elutant, including the saved final wash was titered to measure the number of phage remaining in the elutant.

Amplified phage were then titred to determine their concentration and the process was repeated four times using the amplified phage from the previous round. The phage from the final screening process were sequenced to determine a consensus binding sequence. The titre results were as follows:

Round 1 ($\times 10^3$): Final Wash=100; Elution 1=800; Elution 2=615; Elution 3=411; Elution 4=362; Glycine/Urea combination=100.

Round 2 ($\times 10^2$): Final Wash=2; Elution 1=1400; Elution 3=120; Elution 4=38; Glycine/Urea=75.

Round 3 ($\times 10^3$): Final Wash=7; Elution 1=14,130; Elution 2=5495; Elution 3=1800; Elution 4=1570; Glycine/Urea=3140.

Round 4 was not titred.

In order to demonstrate the effectiveness of the inhibition of calpain by the peptides of this invention, two in situ experiments were conducted using cultured cortical neurons from rat brains to show that the LSEAL peptide inhibited cell death. In the first experiment, cell death of the neurons was induced by exposing the culture to ionomycin. In the second experiment, cell death was induced by exposing the neurons to 30 and 60 $mJ/cm^2$ of UV light. The exposure to either ionomycin or UV light caused calpain I to be activated because of ionomycin-mediated calcium flux or through UV-induced receptors, channels or pore-like structures. Calcein acetoxymethyl ester was used as indicator of live neuron cells while propidium iodide was used an indicator of dead neuron cells.

In the first experiment, ten Samples were prepared. Sample 1 was a control Sample and included the cultured cortical neurons only. A baseline for the average percentage of cell death was determined to be 19%. In Sample 2, 0.4 µM ionomycin was added to the cultured neuron cells to activate calpain I. No LSEAL was added to these Samples. The addition of ionomycin to these Samples caused the percentage of dead cells to more than triple to an average of 68%. Sample 3 was the same as Sample 2 except that 0.00001 micromolar of LSEAL was added before the ionomycin was added. The percentage of dead cells averaged of 106% of no LSEAL. Sample 4 was the same as Sample 3 except that 0.0001 micromolar of LSEAL was added. The percentage of cell death was 83% of no LSEAL. Sample 5 was the same as Sample 4 except that 0.001 micromolar LSEAL was added. The percentage of cell death was 63% of no LSEAL. Sample 6 was the same as Sample 5 except that 0.01 micromolar LSEAL was added. The percentage of cell death was 61% of no LSEAL. Sample 7 was the same as Sample 6 except that 0.1 micromolar LSEAL was added. The percentage of cell death was 57% of no LSEAL. Sample 8 was the same as Sample 7 except that 1.0 micromolar LSEAL was added. The percentage of cell death was 48% of no LSEAL. Sample 9 was the same as Sample 8 except that 10.0 micromolar LSEAL was added. The percentage of cell death was 35% of no LSEAL. Sample 10 was the same as Sample 9 except that 100 micromolar LSEAL was added. The percentage of cell death was 33% of no LSEAL. It is clear from this experiment that the peptide of the invention inhibited calpain I activity. The results are summarized in Table 1 below and the results are graphically illustrated in FIG. 1

TABLE 1

| Micromolar | Percentage Average cell death (ratioed to 0 LSEAL) | Standard Error of the Mean | Number of Samples (n =) | Percent (raw data) |
|---|---|---|---|---|
| 0 LSEAL (Sample 2) | 100 | 4.8 | 13 | |
| .00001 LSEAL (Sample 3) | 106 | 13.0 | 13 | |
| .0001 LSEAL (Sample 4) | 83 | 10.7 | 3 | |
| .001 LSEAL (Sample 5) | 63 | 14.2 | 4 | |
| 0.01 LSEAL (Sample 6) | 61 | 9.4 | 5 | |
| 0.1 LSEAL (Sample 7) | 57 | 5.9 | 7 | |
| 1 LSEAL (Sample 8) | 48 | 4.9 | 4 | |
| 10 LSEAL (Sample 9) | 35 | 3.3 | 6 | |
| 100 LSEAL (Sample 10) | 33 | 8.0 | 3 | |

TABLE 1-continued

| Micromolar | Percentage Average cell death (ratioed to 0 LSEAL) | Standard Error of the Mean | Number of Samples (n =) | Percent (raw data) |
|---|---|---|---|---|
| Cell death percentages raw data: | | | | |
| Control (vehicle treatment only) - Sample 1 | | | | 19 |
| Ionomycin alone - Sample 2 | | | | 68 |

Figure 2:
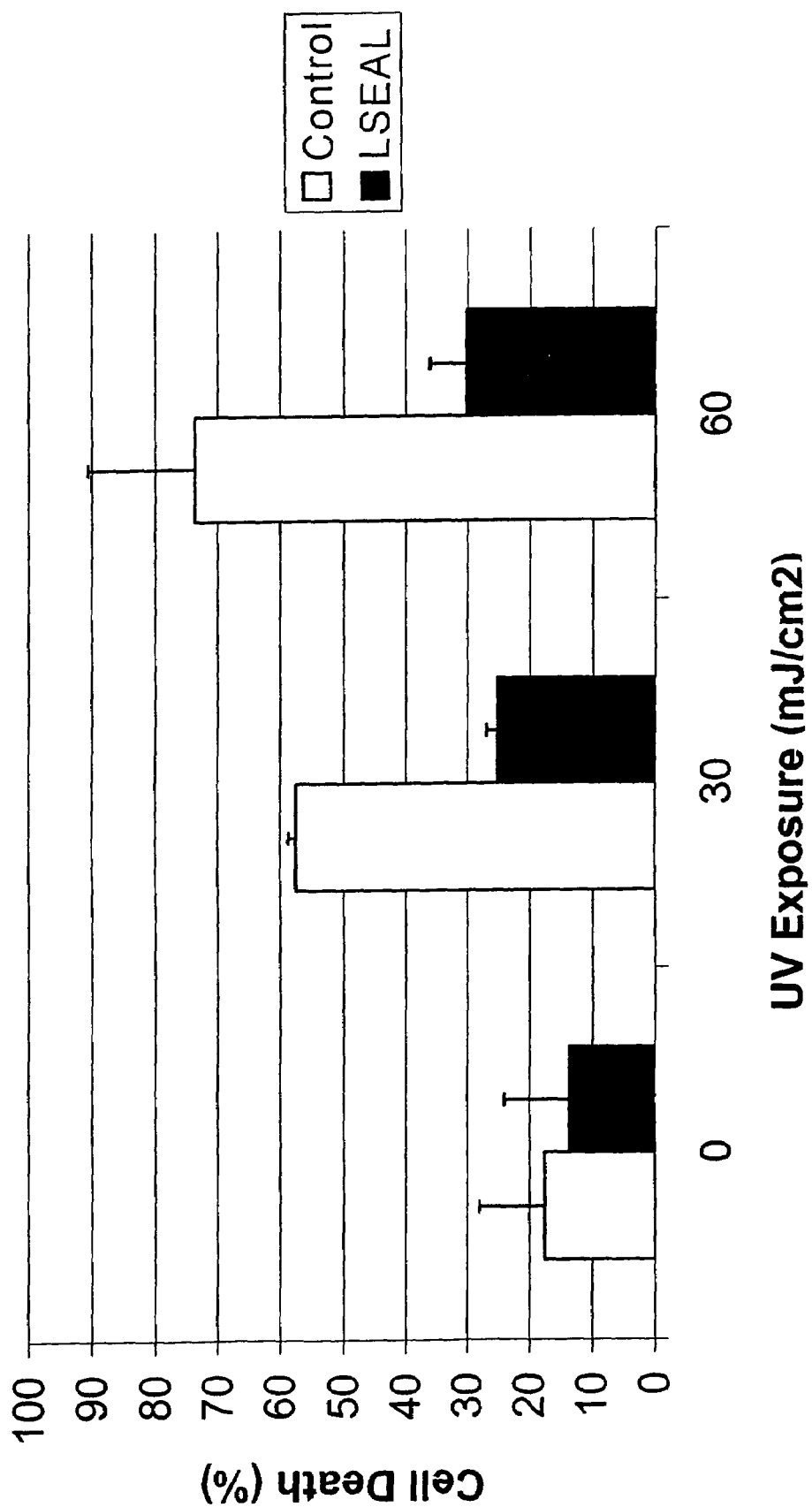
FIG. 2 is a plot of the relationship of ultraviolet light (UV) exposure and cell death between cultured Samples of cortical neurons containing no LSEAL and Samples containing LSEAL.

In the second experiment, cell death of the cultured cortical neurons was induced by UV light. Samples 11, 12 and 13 were control Samples which did not contain any LSEAL. Sample 11 shows the normal % dead cells with no exposure to UV light. The percentage of cell death was 18%. Sample 14 is the same as Sample 11, except for the addition of 100 µM LSEAL to the culture. The percentage of cell death was reduced from 18% to 14%. Sample 12 was exposed to 30 mJ/cm$^2$ of UV light. The percentage of cell death was 58%. The inclusion of the LSEAL before exposure reduced the percentage of cell death to 25%. See Sample 15. If the exposure is increased to 60 mJ/cm$^2$, the cell death percentage is 74% for the culture which does not contain LSEAL (see Sample 13), and 30% for a culture containing LSEAL (see Sample 16). The data clearly show that the peptide of the present invention protects neurons from UV-induced, calpain-dependent cell death. The data for the experiment is set forth below in Tables 3 and 4, and is graphically illustrated in FIG. 2.

TABLE 2

| Sample | Live Cells | Dead Cells | Total Cells | % Dead Cells |
|---|---|---|---|---|
| 11 | 36 | 7 | 43 | 18 |
| 12 | 25 | 33 | 58 | 58 |
| 13 | 17 | 42 | 59 | 74 |
| 14 | 30 | 5 | 35 | 14 |
| 15 | 78 | 26 | 104 | 25 |
| 16 | 56 | 25 | 81 | 30 |

TABLE 3

| UV Light Exposure | Samples | Live Cells | Dead Cells | Total Cells | % Dead Cells | Std Dev |
|---|---|---|---|---|---|---|
| 0 mJ/cm$^2$ | 11 (Control) | 36 | 7 | 43 | 18 | 10 |
| | 14 | 30 | 5 | 35 | 14 | 10 |
| 30 mJ/cm$^2$ | 12 (Control) | 25 | 33 | 58 | 58 | 1 |
| | 15 | 78 | 26 | 104 | 25 | 2 |
| 60 mJ/cm$^2$ | 13 (Control) | 17 | 42 | 59 | 74 | 17 |
| | 16 | 56 | 25 | 81 | 30 | 6 |

Figure 3:
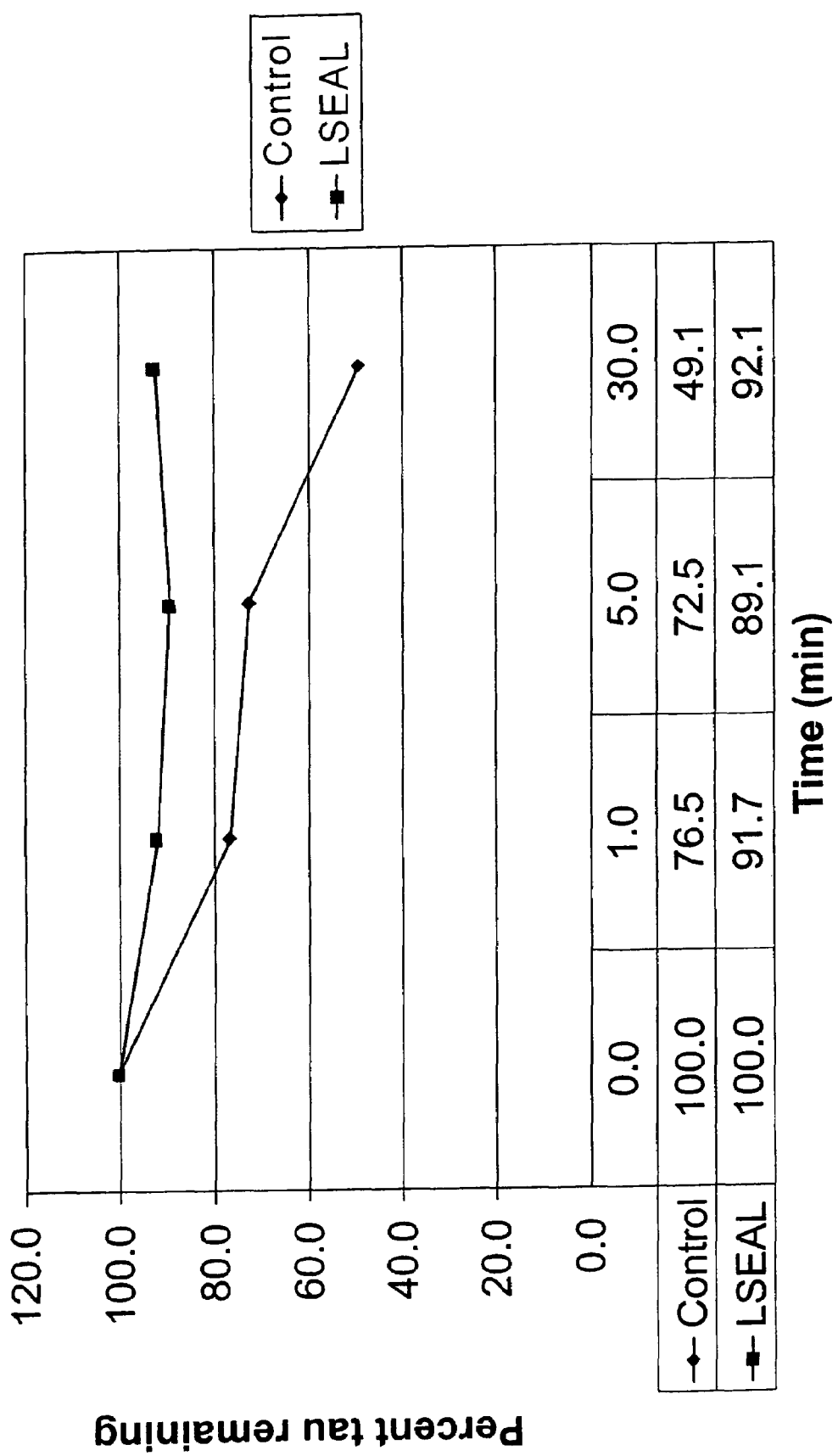
FIG. 3 is a plot of the relationship of the effect of LSEAL on tau degradation by calpain I.

Another experiment was conducted to show the effect of the proteins of the present invention on the tau protein. The tau protein is a microtubule-associated protein (MAP). Tau is a well-described calpain I substrate. The addition of 100 µM LSEAL inhibits degradation of the protein. The results are shown in FIG. 3.

While the salient features have been illustrated and described with respect to particular embodiments, it should be readily apparent that modifications can be made within the spirit and scope of the invention, and it is therefore not desired to limit the invention to the exact details shown and described.

What is claimed is:

1. An isolated 5-mer peptide selected from the group consisting of Leu-Ser-Glu-Ala-Leu (SEQ ID NO:3), Leu-Ala-Asp-Ala-Leu (SEQ ID NO:4), Leu-Phe-Glu-Ala-Leu (SEQ ID NO:5), Leu-Tyr-Asp-Ala-Leu (SEQ ID NO:6), Leu-Leu-Glu-Ala-Leu (SEQ ID NO:7), Leu-Arg-Asp-Ala-Leu (SEQ ID NO:8), Leu-Tyr-Asp-Ala-Met (SEQ ID NO:9), Leu-Thr-Asp-Ala-Leu (SEQ ID NO:10), Ala-Leu-Asp-Ala-Leu (SEQ D NO: 11), Leu-Leu-Asp-Ala-Leu (SEQ ID NO:12), Ala-Ile-Asp-Ala-Leu (SEQ ID NO: 15), Leu-Ile-Asp-Thr-Leu (SEQ ID NO:16), Leu-Ala-Asp-Ser-Leu (SEQ ID NO:17), and Leu-Ser-Asp-Ser-Leu (SEQ ID NO:18).

2. The peptide of claim 1, wherein the peptide inhibits calpain activity towards the substrate tau protein.

3. An isolated peptide consisting of the sequence Leu-Ser-Glu-Ala-Leu (SEQ ID NO:3).

* * * * *